United States Patent [19]

Seliger et al.

[11] 4,433,140

[45] Feb. 21, 1984

[54] TRIDECADEOXYNUCLEOTIDE, PROCESS FOR PREPARATION THEREOF, AND USE THEREOF

[75] Inventors: Hartmut Seliger, Ulm-Lehr, Fed. Rep. of Germany; Eva Rastl; Peter Swetly, both of Vienna, Austria

[73] Assignee: Dr. Karl Thomae GmbH, Biberach an der Riss, Fed. Rep. of Germany

[21] Appl. No.: 351,851

[22] Filed: Feb. 24, 1982

[30] Foreign Application Priority Data

Feb. 25, 1981 [DE] Fed. Rep. of Germany ....... 3106982

[51] Int. Cl.³ ..................... C07H 15/12; C07H 17/00
[52] U.S. Cl. ....................................... 536/27; 536/28; 536/29
[58] Field of Search ............................. 536/27, 28, 29

[56] References Cited

U.S. PATENT DOCUMENTS 4,358,586 11/1982 Rubin .................................. 536/27
4,362,867 12/1982 Paddock .............................. 536/27

OTHER PUBLICATIONS

Mevarech et al., J. Biol. Chem. 254, 7472(1979).
Chem. Abstracts 91 (5)39767j (1979).
Seliger, European J. Cell. Biol. 25 (1), 1981, pp. 8-9.

Primary Examiner—Ethel G. Love
Attorney, Agent, or Firm—Oblon, Fisher, Spivak, McClelland & Maier

[57] ABSTRACT

A tridecadeoxynucleotide of the formula dCCTTCTGGAACTG, is useful as a primer in the enzymatic synthesis of deoxyribonucleic acid (DNA) on messenger ribonucleic acid (mRNA) matrices.

The new tridecadeoxynucleotide is obtained by linking suitable partially protected oligonucleotide blocks, particularly two suitable oligonucleotide fragments, e.g. by linking a suitable tetramer to a suitable nomaer, using a condensing agent.

1 Claim, 1 Drawing Figure

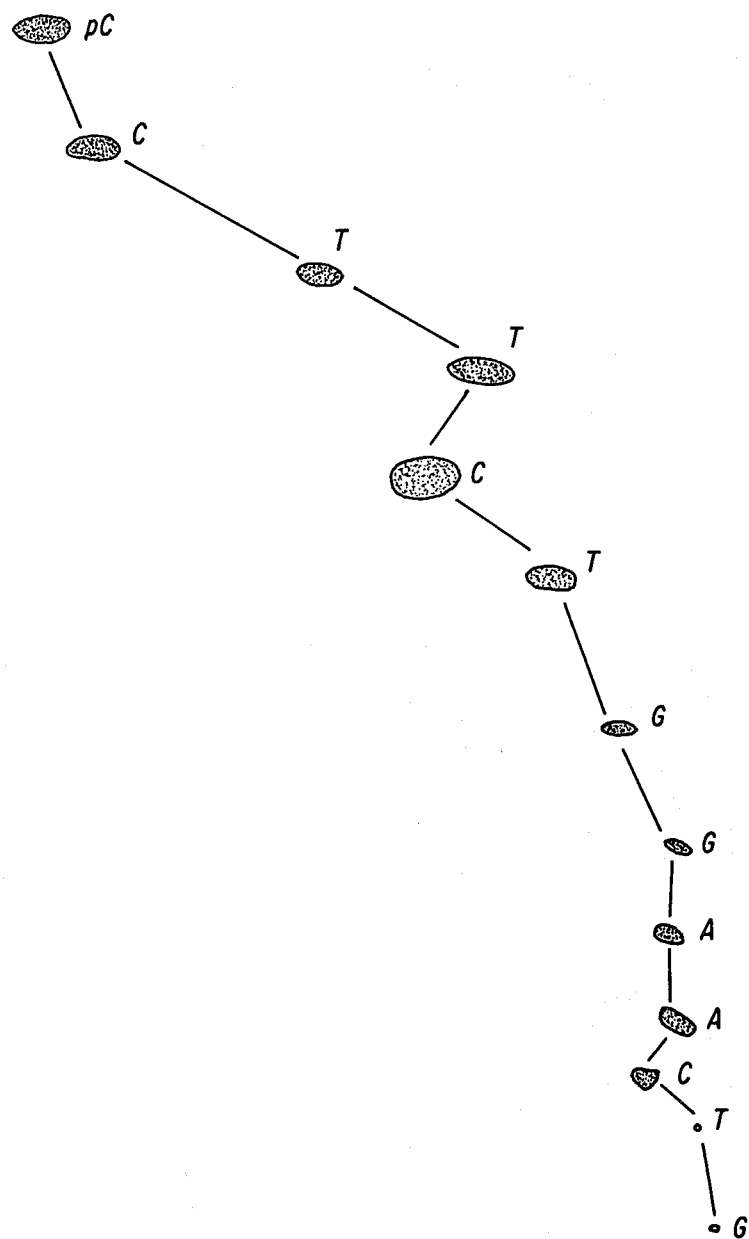

TRIDECADEOXYNUCLEOTIDE, PROCESS FOR PREPARATION THEREOF, AND USE THEREOF

BACKGROUND OF INVENTION

1. Field of the Invention

This invention relates to polynucleotides and more particularly to polynucleotides useful as primers in synthesizing deoxyribonucleic acids.

2. Description of the Prior Art

Highly purified interferom is only available for clinical trials in extremely small quantities. To permit the production of larger quantities of interferon and thus meet this need, human interferon is now synthesised in bacteria using genetic engineering methods (see S. Nagata, H. Taira, A. Hall, L. Johnsrud, M. Streuli, J. Esco i, W. Boll, K. Cantell and C. Weissmann in Nature 284, 316 (1980)).

For this, the gene which codes the protein sequence of the human leucocyte interferon which is to be produced has to be transferred into a bacterium in a suitable way so as to permit expression of the gene and hence synthesis of the human interferon in the bacterium. The procedure used is to integrate the corresponding deoxyribonucleic acid sequence in a self-replicating vector (preferably a bacterial plasmid or a bacterial virus) and then to introduce the genetic material modified in this way into the bacterial cell. To enable expression of this foreign gene to occur, the deoxyribonucleic acid sequence must be incorporated in the vector in the correct orientation and in the correct reading frame.

The nucleic acid suitable for this gene manipulation is appropriately selected on the messenger ribonucleic acid level (mRNA level), i.e. in order to recover the required DNA, the procedure is to synthesise the DNA which is complementary to the mRNA by means of an enzyme, known as reverse transcriptase. To initiate this enzymatic synthesis, a so-called primer is required, a fragment of DNA the base sequence of which is complementary to a portion of the mRNA in question and which, after being added to the mRNA, becomes bound to this complementary portion in the form of a hybrid double strand.

If the mRNA in question has portions containing poly-A, oligo-dT would be suitable as the primer. However, since the "correct" mRNA is not present in pure form but occurs in admixture with other mRNA sequences, this would initiate the transcription of all the mRNA sequences containing poly-A, and this would result in a complex mixture of DNA fragments which would not be suitable for the purpose specified above.

If, on the other hand, a deoxyoligonucleotide fragment which is complementary to a specific base sequence of the "correct" mRNA is used as the primer, there is a greater probability that only this one desirable transcription will occur, even in the presence of various other mRNAs, and hence the desired complementary DNA will be synthesised in a substantially pure state in the reverse transcriptase reaction.

The following application is based on the finding (see T. Taniguchi, N. Mantei, M. Schwarzstein, S. Nagata, M. Muramatsu and C. Weissmann in Nature 285, 547 (1980)), that all the interferon genes known at present have a common sequence consisting of thirteen nucleotides, which codes the amino acids nos. 47-50.

A sequence of thirteen nucleotides can be bound in stable fashion, in the form of a hybrid double strand (see M. Mevarech, B. E. Noyes and K. L. Agarwal in J. Biol. Chem. 254, 7472 (1979)) to all mRNA molecules which contain a sequence complementary thereto, but not to the mRNA molecules which occur predominantly in the present mixture and which do not contain this specific sequence. Therefore, if a specific DNA sequence of this kind is used as primer in the reverse transcriptase reaction, this results in a selection of the interferon-specific species of mRNA in the mixture of different nRNAs, and the probability of thus obtaining interferon-specific complementary DNA which is free from noninterferon-specific DNA is increased considerably.

Hence a need has continued to exist for a suitable primer for synthesis of DNA coding for interferon on an interferon mRNA matrix.

SUMMARY OF THE INVENTION

Accordingly it is an object of the invention to provide a primer for synthesis of DNA which codes for interferon.

Further objects of the invention will become apparent from the following disclosure.

The objects of the invention are achieved by a new tridecadeoxynucleotide of formula

a process for the preparation thereof and the use thereof, particularly as a primer in the enzymatic synthesis of deoxyribonucleic acid (DNA) on messenger ribonucleic acid (mRNA) matrices.

According to the invention, the new tridecadeoxynucleotide is obtained by linking suitable partially protected oligonucleotide blocks, particularly two suitable oligonucleotide fragments, e.g. by linking a suitable tetramer to a suitable nonamer, using a condensing agent.

BRIEF DESCRIPTION OF THE DRAWINGS

The single FIGURE represents a "fingerprint" analysis of the tridecamer produced by the procedure of Example 1, by electrophoresis of fragments of the tridecamer in polyacrylamide gel.

DETAILED DESCRIPTION OF THE INVENTION AND PREFERRED EMBODIMENTS

An acid-activating or dehydrating agent such as a sulfonyl tetrazolide, sulfonyl triazolide, sulfonyl imidazolide, sulfonyl chloride or carbodiimide, e.g. mesitylenesulfonyl tetrazolide or N,N'-dicyclohexylcarbodiimide may be used as the condensing agent.

Suitable protecting groups are, for example, for the 5'-terminal OH group, preferably an acid-cleavable protecting group such as a trityl, monomethoxytrityl, dimethoxytrityl, 1-ethoxyethyl or 4-methoxytetrahydropyran-4-yl group, or, for the phosphate group, the trichloroethyl, cyanoethyl or p-chlorophenyl group and, for the amino functions of the bases, the isobutyloxy/carbonyl, benzoyl, anisoyl or isobutyryl group.

The reaction is effected in a solvent, preferably in an anhydrous solvent, e.g. in absolute pyridine, in the presence of a condensing agent, preferably mesitylenesulfonyl tetrazolide, at temperatures of between 0° and 50° C., but preferably at ambient temperature.

Then the protecting groups are split off from the fully protected tridecamer thus obtained. Thus, an acid-cleavable protecting group, such as the dimethoxy trityl group, is split off in a solvent, e.g. in methanol/chloroform, and in the presence of an acid such as benzenesulfonic acid, appropriately at 0° C., and subsequently the other protecting groups, e.g. the benzoyl, isobutyryl or p-chlorophenylphosphoryl groups, are split off by treating with a base, e.g. pyridine/conc. ammonia, at temperatures of between 20° and 80° C., but preferably first at 35° C. and then at 55° C.

The following examples are intended to illustrate the invention more fully:

PREPARATION OF THE STARTING PRODUCTS

Key

DMTr = p,p'-dimethoxy-triphenylmethyl
p. = p-chlorophenylphosphoryl
CE = β-cyanoethyl
ibu = isobutyryl
bz = benzoyl (on the base nitrogen)
Bz = benzoyl (on the furanyl oxygen)
DTT = dithiothreitol
EDTA = ethylenediamine tetraacetate
RNA = ribonucleic acid
DNA = deoxyribonucleic acid
dNTP = mixture of 4 deoxynucleotide triphosphates of adenosine, thymidine, guanosine and cytidine
cDNA = DNA which is complementary to the messenger RNA

EXAMPLE A

5'-Dimethoxytrityldeoxythymidine-3'-p-chlorophenyl-β-cyanoethyl phosphate DMTrdTp. (CE)

1.59 g (3 mmol) of 5'-dimethoxytrityl-thymidine (prepared according to H. Schaller et al., J. Amer. chem. Soc. 85, 3821 (1963)) are dissolved in about 20 ml of absolute acetonitrile. To remove any traces of water, 3 to 4 ml of acetonitrile are drawn off several times and replaced by absolute acetonitrile (to make the solution absolute).

The dry solution is mixed with 1 ml (about 12.5 mmol) of N-methyl-imidazole. 2.8 g (10 mmol) of p-chlorophenyl-β-cyanoethyl-phosphoryl chloride, dissolved in 5 ml of absolute acetonitrile, are slowly added dropwise, with cooling. The mixture is left to react for 2 hours at 20° C., after which thin layer chromatography is carried out, showing that the mixture has reacted completely to form the above-mentioned product.

In order to stop the reaction, the mixture is cooled in an ice bath and then 5 ml of 1 M ammonium hydrogen carbonate solution are slowly added dropwise. The mixture is left to stand at ambient temperature for 1 hour. Then it is concentrated by evaporation in the rotary evaporator, taken up in 20 ml of chloroform and washed three times with about the same volume of 0.1 M ammonium hydrogen carbonate solution and finally washed once with the same volume of water. The chloroform phase is dried over sodium sulfate, filtered and concentrated in the rotary evaporator. The residue is substantially pure 5'-dimethoxytrityldeoxythymidine-3'-p-chlorophenyl-β-cyanoethyl phosphate. To purify it further, the compound is chromatographed by preparative liquid chromatography (prep-LC 500, Waters) on a silica gel column with 2.5% methanol in methylene chloride.

Yield: 1.8 g (about 80% of theory).
Characteristics:

UV in methanol: $\lambda_{max}=268$ nm; $\lambda_{min}=250$ nm, in perchloric acid/ethanol 9:1: $\lambda_{max}=500$ nm;
$A_{280}/A_{500}=0.13$
$r_f$ by TLC on silica gel
with chloroform/methanol 9:1 = 0.48
with chloroform/ethanol 1:1 = 0.77
with chloroform/methanol 9:1, after 6 hours' treatment with triethylamine, $R_f$ of 0.48 after being 0.0; after treatment with 2% benzenesulfonic acid in chloroform/methanol 7/3, $R_f$ of 0.48 after being 0.26.

EXAMPLE B $N^2$, $O^3$, $O^{5'}$-triisobutyryl-deoxyguanosine $dG^{ibu}$ 2.67 g (10 mmol) of deoxyguanosine (prepared analogously to the method described by H. G. Khorana et al., J. Mol. Biol. 72, 251 (1972)) are suspended in dioxan and lyophilised. The deoxyguanosine predried in this way is further dried by suspending three times in pyridine, each time in 10 ml of absolute pyridine. Then a suspension in a mixture of 60 ml of chloroform and 7 ml of pyridine is prepared. 8 ml (80 mmol) of isobutyric acid chloride are slowly added dropwise to this suspension, with cooling and stirring. The suspension slowly changes into a clear solution. After 2 hours' reaction, the solution is mixed with 20 ml of water or, alternatively, 0.1 M of ammonium hydrogen carbonate solution, with cooling. The organic phase is concentrated in the rotary evaporator until a viscous, rubbery residue is obtained which is then taken up in 100 ml of ethanol. Thin layer chromatographyt on silica gel in ethanol/chloroform (1:1) shows total conversion of the deoxyguanosine into $N,O^{3'},O^{5'}$-triisobutyryl-deoxyguanosine.

The ethanolic solution of the intermediate product is treated with 100 ml of 2 N sodium hydroxide solution at 0° C. for 15 minutes, then rapidly neutralised with Dowex 50 ion exchanger (pyridinium form). The ion exchanger is filtered off and washed thoroughly with methanol/pyridine and a warm methanol/water mixture. The wash solutions are combined with the filtrate. The combined solutions are evaluated to dryness in the rotary evaporator. The residue is dissolved in hot water; it crystallises on cooling.

Yield: 2.7 g (80% of theory).
Characteristics:
UV in methanol: $\lambda_{max}=280$ nm and broad maximum at 254–260 nm; $\lambda_{min}=272$, 227 nm
$A_{260}/A_{280}=1.36$

EXAMPLE C (a) 5'-Dimethoxytrityl-$N^2$-isobutyryl-deoxyguanosine DMTrdG$^{ibu}$ 2.7 g (8 mmol) of $N^2$-isobutyryldeoxyguanosine and 2.85 g (8.5 mmol) of dimethoxytrityl chloride are reacted for 2 hours at ambient temperature in 20 ml of absolute pyridine, with the addition of a small quantity of 4-dimethylaminopyridine (DMAP) as catalyst. The conversion is checked by TLC on silica gel in ethanol/chloroform 1:1. If the conversion is not complete, the reaction may be continued for a further hour, by adding a further 0.5 mmol of dimethoxytrityl chloride. Then 20 ml of ice-cooled water are added. The water-pyridine solution is extracted three times, each time with 30 ml of chloroform. The chloroform phase is dried over sodium sulfate, filtered and concentrated in the rotary evaporator, with the addition of toluene, in order to remove the pyridine. The residue is taken up in a little chloroform and separated by preparative liquid chromatography on silica gel with 4% methanol in methylene chloride Yield: 4 g (80% of theory).

Characteristics:

UV in methanol: $\lambda_{max}=277$, 255–260 nm; $\lambda_{min}=272$, 235 nm.

in perchloric acid/ethanol 9:1: $\lambda_{max}=500$ nm; $A_{260}/A_{500}=0.26$ $R_f$ by TLC on silica gel
with chloroform/methanol 9:1=0.28
with chloroform/methanol 1:2=0.65

(b) 5'-Dimethoxytrityl-N$^2$-isobutyryl-deoxyguanosine-3'-p-chlorophenyl-$\beta$-cyanoethylphosphate DMTrdG$^{ibu}$p. (CE)

The compound is prepared analogously to Example A starting from 5'-dimethoxytrityl-N$^2$-isobutyryldeoxyguanosine. Monitoring of the reaction by TLC in chloroform/ethanol 1:1 shows complete conversion. The product is highly purified by preparative liquid chromatography on silica gel using 3.5% methanol in methylene chloride and a yield of 3.6 g (81% of theory) of pure product is obtained, from a mixture containing 5 mmol of starting material.

Characteristics:

UV in methanol: $\lambda_{max}=277$, 254–260 nm; $\lambda_{min}=272$, 235 nm in perchloric acid/ethanol 9:1;

$A_{280}/A_{500}=0.27$ $R_f$ by TLC on silica gel
with chloroform/methanol 9:1=0.43
with chloroform/ethanol 1:1=0.62.

EXAMPLE D

5'-Dimethoxytritryl-N$^4$-benzoyl-deoxycytidine-3'-p-chlorophenyl-$\beta$-cyanoethyl-phosphate DMTrdC$^{bz}$p. (CE)

The compound is prepared analogously to Example A starting from 5'-dimethoxytrityl-N$^4$-benzoyl-deoxycytidine (prepared according to H. Schaller et al., J. Mer. chem. Soc. 85, 3821 (1963)), then highly purified by preparative liquid chromatography on silica gel with 2.5% methanol in methylene chloride. The reaction is monitored by TLC using chloroform/methanol 9:1 and indicates total conversion of the starting material. For further purification, the product was chromatographed by preparative liquid chromatography on a silica gel column using 2% methanol in methylene chloride.

Yield: 85% of theory.

Characteristics:

UV in methanol: $\lambda_{max}=305$, 260 nm; $\lambda_{min}=285$, 240 nm $R_f$ by TLC on silica gel
with chloroform/methanol 9:1=0.67.

EXAMPLE E

5'-Dimethoxytrityl-N$^6$-benzoyldeoxyadenosine-3'-p-chlorophenyl-$\beta$-cyanoethylphosphate DMTrdA$^{bz}$p. (CE)

The compound is prepared analogously to Example A starting from 5'-dimethoxytrityl-N$^6$-benzoyldeoxyadenosine (prepared according to H. Schaller et al., J. Amer. Chem. Soc. 86, 3821 (1963)), and the product is highly purified by preparative liquid chromatography on silica gel with 3.5% methanol in methylene chloride. Monitoring of the reaction by TLC using chloroform/methanol 9:1 shows complete conversion of the starting material. For further purification, the product is chromatographed by preparative liquid chromatography on a silica gel column using 2.5% methanol in methylene chloride.

Yield: 80% of theory

Characteristics:

UV in methanol: $\lambda_{max}=280$ nm; $\lambda_{min}=256$ nm.

$R_f$ by TLC on silica gel with chloroform/methanol 9:1=0.63.

EXAMPLE F

N$_2$-Isobutyryl-O$^3$'-benzoyl-deoxyguanosine

N$^2$-isobutyryl-deoxyguanosine (see Example B) is dissolved in 15 ml of absolute pyridine. 1.2 mmol of benzoyl chloride are slowly added dropwise thereto, while the mixture is cooled to 0° C. The reaction is finished in 4 hours (checked by TLC on silica gel using chloroform/methanol 9:1). Then 10 ml of water or 0.1 M ammonium hydrogen carbonate solution are added to the reaction mixture. The mixture is then extracted three times with chloroform. The chloroform extracts are reextracted several times with water and then dried over sodium sulfate. The chloroform solution is filtered, concentrated by evaporation and then brought to dryness with toluene, in the rotary evaporator, in order to remove the pyridine.

In order to remove the dimethoxytrityl protecting group, the residue is then treated in a mixture of 2% benzene sulphonic acid in chloroform/methanol 7:3 for 3 minutes at 0° C. Then 5 ml of 5% ammonium hydrogen carbonate solution are added. The chloroform phase is dried, filtered, concentrated by evaporation and purified by preparative liquid chromatography on silica gel using 3.5% methanol in methylene chloride.

Yield: 80% of theory.

Characteristics:

UV in methanol: $\lambda_{max}=277$, 255–260 nm; $\lambda_{min}=272$, 235 nm.

$R_f$ by TLC on silica gel with chloroform/methanol 9:1=0.20.

EXAMPLE G

Cleaving the dimethoxytrityl group from dimethoxytritylnucleoside-3'-p-chlorophenyl-$\beta$-cyanoethyl phosphate The starting compound is mixed with a 2% solution of benzene sulfonic acid in chloroform/methanol (7:3), while cooling with ice, and stirring for 3 to 4 minutes. Then the mixture is neutralised by the addition of 5% ammonium hydrogen carbonate solution. The organic phase is separated off and the aqueous phase is extracted once with chloroform. The combined chloroform phase is dried and concentrated by evaporation in the rotary evaporator. The residue is dissolved in a little chloroform and purified either on a silica gel column ("short column", diameter: length=about 1:5 to 1:8; eluant: chloroform+0–7% methanol) or by preparative liquid chromatography on silica gel (eluant: chloroform/methanol, methanol content determined by preliminary HPLC test).

Yield: 80–90% of theory.

The detritylated monomers are stored at −20° C., dissolved in chloroform.

EXAMPLE H

Cleaving the β-cyanoethyl group from dimethoxytrityl nucleoside-3'-p-chlorophenyl-β-cyanoethyl phosphate The quantity of starting compound required for the condensation is dissolved in a little pyridine, made absolute and treated with a 50- to 100-fold excess of triethylamine. After 2 to 6 hours, the β-cyanoethyl group has been quantitatively split off (checked by TLC on silica gel using chloroform/methanol 9:1; product has $R_f=0.0$). Any excess triethylamine and the acrylonitrile formed are removed in vacuo. The residue is taken up in a little absolute pyridine.

EXAMPLE I

N²-Isobutyryl-deoxyguanosine-3'-p-chlorophenylphosphoryl-5'-(N²-isobutyryl)-deoxyguanosine-3'-p'chlorophenyl-β-cyanoethylphosphate dG$^{ibu}$p.G$^{ibu}$p. (CE)

0.6 mmol of 5'-dimethoxytrityl-N²-isobutyryldeoxyguanosine-3'-p-chlorophenylphosphate are dissolved in 10 ml of absolute pyridine and further dried several times. A similarly pre-treated pyridine solution of 0.4 mmol of N²-isobutyryl-deoxyguanosine-3'-p-chlorophenyl-β-cyano-ethylphosphate is added and the mixture is evaporated down to a volume of about 10 ml. Then 1.5 mmol of mesitylenesulfonyl tetrazolide are added and again some pyridine is drawn off. The conversion is checked by TLC on silica gel using chloroform/methanol 9:1, first after 30 minutes' reaction at ambient temperature. After 45 minutes, the thin layer chromatogram shows that the hydroxyl component dG$^{ibu}$p. (CE) has disappeared. Condensation is immediately stopped, using 10 ml of 5% ammonium hydrogen carbonate solution, while cooling with ice, and the reaction mixture is left to stand for 1 hour at ambient temperature.

In order to work it up, the mixture is extracted twice, each time with 10 mol of chloroform. The combined chloroform phases are washed once with 0.1 M ammonium hydrogen carbonate solution and once with 10 ml of water. Then the chloroform solution is dried with sodium sulfate and concentrated by evaporation in the rotary evaporator. Any residual pyridine is eliminated from the solution by evaporating several times in the rotary evaporator with toluene and methanol. The residue is crude 5'-dimethoxytrityl-N²-isobutyryl-deoxyguanosine-3'-chlorophenylphosphoryl-5'-(N²-isobutyryl)deoxyguanosine-3'-p-chlorophenyl-β-cyanoethylphosphate.

If purification is to be effected at this stage of the product, the residue is taken up in a little chloroform and then chromatographed either on a silica gel "short column" (e.g. silica gel 60, Merck no. 7733 or 7734 and equivalent types of silica gel made by other companies) in chloroform with a gradient of 0–7% methanol or in a preparative LC system with a silica gel column, using a chloroform/methanol mixture as the eluant, the composition of which has previously been determined by analytical HPLC.

The tritylated oligomers are characterised by their UV spectrum in methanol ($\lambda_{max}$ and $\lambda_{min}$ like the detritylated derivative, see below) and in perchloric acid/ethanol 9:1 ($\lambda_{max}=500$ nm; measurement of $A_{280}/A_{500}$) and by their $R_f$ values by TLC on silica gel using chloroform/methanol 9:1.

Cleaving the dimethoxytrityl protecting group:

The dimethoxytrityl protecting group may be split off, without purification of the above-mentioned intermediate product, in the following manner: the residue from the workup is treated at 0° C. for 3 minutes with a 2% solution of benzenesulphonic acid in chloroform/methanol 7:3 and then rapidly neutralised with 10 ml of 5% ammonium hydrogen carbonate solution. The phases are separated and the aqueous phase is extracted again with 10 ml of chloroform. The combined chloroform phases are dried over sodium sulphate, filtered and concentrated by evaporation. The concentrate is added to a silica gel column (2×7 cm, silica gel 0.2–0.5 mm made by Macherey-Nagel or Merck No. 7733). The product is eluted with chloroform+0–9% methanol (concentration of methanol increased step by step; flow rate 80 to 100 ml/hour; 15 ml fractions; separation monitored by thin layer chromatography on silica gel in chloroform/methanol 9:1). The fractions of product are combined, evaporated in the rotary evaporator, dissolved in a measured volume of chloroform and stored at $-20°$ C.

Yield: 62% of theory.
Characteristics:
UV in methanol: $\lambda_{max}=277$, 262–255 nm; $\lambda_{min}=272$, 235 nm
$A_{260}/A_{280}=1.38$
$R_f$ values by TLC on silica gel
with chloroform/methanol 9:1=0.15
with chloroform/methanol 8:2=0.52

Cleaving the β-cyanoethyl protecting group:

If oligomers of the 5'-dimethoxytrityl-nucleoside¹-3'-p-chlorophenylphosphoryl-5'-nucleoside²-3'-p-chlorophenyl phosphate type are required, the purified tritylated oligomers are used as starting materials and the β-cyanoethyl protecting group is split off analogously to Example H. The product can be used without further purification; the yield of the decyanoethylation is virtually quantitative. The product is characterised as described hereinbefore for the tritylated dimers.

The following compounds were prepared analogously:

5'-Dimethoxytrityl-N⁴-benzoyl-deoxycytidine-3'-p-chlorophenyl-phosphoryl-5'-(N⁴-benzoyl-)deoxycytidine-3'-p-chlorophenylphosphate (abbreviation: DMTrdC$^{bz}$p.C$^{bz}$p.−) Deoxythymidine-3'-p-chlorophenylphosphoryl-5'-deoxythymidine-3'-p-chlorophenyl-β-cyanoethyl-phosphate dTp.Tp. (CE)) (abbreviation: dTp.Tp. (CE))

5'-Dimethoxytrityl-N⁴-benzoyl-deoxycytidine-3'-p-chlorophenylphosphoryl-5'-deoxythymidine-3'-p-chlorophenyl-phosphate (abbreviation: DMTrdC$^{bz}$p.Tp.−)

5'-Dimethoxytrityl-N⁶-benzoyl-deoxyadenosine-3'-p-chlorophenylphosphoryl-5'-(N⁶-benzoyl-)deoxyadenosine-3'-p-chlorophenylphosphate (abbreviation: DMTrda$^{bz}$p.A$^{bz}$p.−)

Deoxythymidine-3'-p-chlorophenylphosphoryl-5'-(N²-isobutyryl-O³'-benzoyl-)deoxyguanosine (abbreviation: dTp.G$_{Bz}{}^{ibu}$)

EXAMPLE K

DMTrdC$^{bz}$p.Tp.G$_{Bz}{}^{ibu}$ 0.27 mol of DMTrdC$^{bz}$p.− are dissolved in 10 ml of absolute pyridine and rendered absolute by treating several times with pyridine. Then 0.18 mmol of dTp.G$_{Bz}{}^{ibu}$ are added and the mixture is again made absolute. Then 0.7 mmol of mesitylenesulfonyl tetrazolide are added and again some pyridine is drawn off. The reaction is carried out for 2 hours at ambient temperature.

The stopping of the reaction and the processing of the product are effected as in Example I.

The crude product is taken up in a little chloroform and separated by column chromatography (column: 2×10 cm; silica gel 60, Merck No. 7733; eluant: chloroform+0–5% methanol).

Yield: 65% of theory.

The dimethoxytrityl protecting group is split off analogously to Example I.

Yield: 80% of theory.

Characteristics:

UV in methanol: $\lambda_{max}=258$ nm; $\lambda_{min}=247$ nm.

EXAMPLE L

DMTrdC$^{bz}$p.Tp.G$^{ibu}$p.G$^{ibu}$p.−

0.2 mmol of DMTrdC$^{bz}$p.Tp. (prepared analogously to Example I) are dissolved in 10 ml of absolute pyridine and rendered absolute by treating several times with pyridine. Then 0.092 mol of dG$^{ibu}$p.G$^{ibu}$p. (CE) in pyridine are added, with further drying, followed by 0.4 mmol of mesitylenesulfonyl tetrazolide. The reaction is carried out for 1½ hours at ambient temperature.

The termination of the reaction and the workup of the product are effected analogously to Example I.

The crude product is taken up in a little chloroform and separated by column chromatography (column: 2×10 cm; silica gel 60, Merck No. 7733; eluant: chloroform+0–7% methanol).

Decyanoethylation as described in Example H.

Yield: 75% of theory.

Characteristics:

UV in methanol: $\lambda_{max}=260$ nm; $\lambda_{min}=244$ nm.

The following compounds were prepared analogously:

DMTrdC$^{bz}$p.C$^{bz}$p.Tp.Tp.−

DMTrdC$^{bz}$p.Tp.G$^{ibu}$p.G$^{ibu}$p.−

EXAMPLE M dA$^{bz}$p.A$^{bz}$p.C$^{bz}$p.Tp.G$_{Bz}$$^{ibu}$ 0.75 mmol DMTrdA$^{bz}$p.A$^{bz}$p.− are dissolved in 10 ml of absolute pyridine and rendered absolute by treating several times with pyridine. Then 0.177 mmol of dC$^{bz}$p.Tp.G$_{Bz}$$^{ibu}$ in pyridine is added, with further drying, followed by 0.55 mmol of mesitylenesulfonyl tetrazolide. The reaction is effected for 2½ hours at ambient temperature.

Termination of the reaction and workup of the product are effected analogously to Example I.

The crude product is taken up in a little chloroform and separated by column chromatography (column: 2×10 cm; silica gel 60, Merck No. 7733; eluant: chloroform+0–5% methanol).

Yield: 80% of theory.

Characteristics: UV in methanol: $\lambda_{max}=295$ (shoulder), 263 nm; $\lambda_{min}=255$ nm.

Detritylation is effected analogously to Example G. The product is used for further experiments without any further column separation.

EXAMPLE N dC$^{bz}$p.Tp.G$^{ibu}$p.G$^{ibu}$p.A$^{bz}$p.A$^{pz}$p.C$^{bz}$p.Tp.G$_{Bz}$$^{ibu}$ 0.024 mmol of DMTrdC$^{bz}$p.Tp.G$^{ibu}$p.G$^{ibu}$p.− are dissolved in 5 ml of absolute pyridine and rendered absolute by treating several times with pyridine. Then 0.016 mmol of dA$^{bz}$p.A$^{bz}$p.C$^{bz}$p.Tp.G$_{Bz}$$^{ibu}$ in pyridine are added, with further drying, followed by 0.2 mmol of mesitylenesulfonyl tetrazolide. The reaction is effected for 2 hours at ambient temperature.

Termination of the reaction and workup of the product are effected analogously to Example I.

The dimethoxytrityl group is split off from the crude product analogously to Example G.

The crude material thus obtained is taken up in a little chloroform and applied to a TLC aluminium film (20×20 cm, Merck silica gel 60/F$_{254}$) and the chromatogram is developed with chloroform/methanol 9:1. The zone of product situated at R$_f$=about 0.2 is cut out and eluted in a line elution apparatus (Desaga) with chloroform/methanol 1:1. The eluate is evaporated to dryness.

Yield: 34% of theory.

Characteristics:

UV in methanol: $\lambda_{max}=258$ nm; $\lambda_{min}=240$ nm

EXAMPLE O dG$^{ibu}$p.A$^{bz}$p. (CE)

Prepared analogously to Example I by reacting 1.5 mmol of DMTrdG$^{ibu}$p.− and 1 mmol of dA$^{bz}$p. (CE) with 3.8 mmol of mesitylenesulfonyl tetrazolide.

Yield: 36% of theory.

Characteristics:

UV in methanol; $\lambda_{max}=276$ nm; $\lambda_{min}=267$ nm

R$_f$ by TLC on silica gel with chloroform/methanol 9:1=0.21 and 0.30 (diastereoisomers).

EXAMPLE P

DMTrdA$^{bz}$p.C$^{bz}$p. (CE)

Prepared analogously to Example I by reacting 0.8 mmol of DMTrdA$^{bz}$p− and 0.6 mmol of dC$^{bz}$p. (CE) with 2.4 mmol of mesitylenesulfonyl tetrazolide.

Yield: 73% of theory.

Characteristics:

UV in methanol: $\lambda_{max}=263$ nm, $\lambda_{min}=248$ nm

R$_f$ by TLC on silica gel with chloroform/methanol 9:1=0.57

EXAMPLE Q

DMTrdG$^{ibu}$p.G$^{ibu}$p.A$^{bz}$p.−

Prepared analogously to Example I by reacting 0.2 mmol of DMTrdG$^{ibu}$.p− and 0.144 mmol of dG$^{ibu}$p.A$^{bz}$p. (CE) with 0.6 mmol of mesitylenesulfonyl tetrazolide.

Yield: 60% of theory.

Characteristics:

UV in methanol: $\lambda_{max}=278$ nm, $\lambda_{min}=268$ nm

R$_f$ by TLC on silica gel with chloroform/methanol 9:1=0.21

EXAMPLE R dTp.Tp.C$^{bz}$p.Tp. (CE)

Prepared analogously to Example L by reacting 0.1 mmol of DMTrdTp.Tp.− and 0.07 mmol of dC$^{bz}$p.Tp. (CE) with 0.3 mmol of mesitylenesulfonyl tetrazolide.

Yield: 30% of theory.

Characteristics:

UV in methanol: $\lambda_{max}=262$ nm, $\lambda_{min}=\lambda_{min}=243$ nm

R$_f$ by TLC on silica gel with methanol/chloroform 9:1=0.30.

EXAMPLE S dA$^{bz}$p.C$^{bz}$p.Tp.G$_{Bz}$$^{ibu}$

Prepared analously to Example L by reacting 0.2 mmol of DMTrdA$^{bz}$p.C$^{bz}$p.⁻ and 0.14 mmol of dTp.G$_{Bz}$$^{ibu}$ with 0.6 mmol of mesitylenesulfonyl tetrazolide.

Yield: 61% of theory.
Characteristics:
UV in methanol: $\lambda_{max}$=262 nm; $\lambda_{min}$=247 nm
R$_f$ by TLC on silica gel
with chloroform/methanol 9:1=0.46.

EXAMPLE T

DMTrdC$^{bz}$p.C$^{bz}$p.Tp.Tp.C$^{bz}$p.Tp.⁻

Prepared analogously to Example N by reacting 0.035 mmol of DMTrdC$^{bz}$p.C$^{bz}$p.⁻ with 0.021 mmol of dTp.Tp.C$^{bz}$p.Tp. (CE) and 0.2 mmol of mesitylenesulfonyl tetrazolide.

Yield: 75% of theory.
Characteristics:
UV in methanol: $\lambda_{max}$=262 nm; $\lambda_{min}$=247 nm
R$_f$ by TLC on silica gel
with chloroform/methanol 9:1=0.48.

EXAMPLE U dG$^{ibu}$p.G$^{ibu}$p.A$^{bz}$p.A$^{bz}$p.C$^{bz}$p.Tp.G$_{Bz}$$^{ibu}$ Prepared analogously to Example N by reacting 0.036 mmol of DMTrdG$^{ibu}$p.G$^{ibu}$p.A$^{bz}$p.⁻ with 0.022 mmol of dA$^{bz}$p.C$^{bz}$p.Tp.G$_{Bz}$$^{ibu}$ and 0.2 mmol of mesitylenesulfonyl tetrazolide.

Yield: 25% of theory
Characteristics:
UV in methanol: $\lambda_{max}$=278 nm; $\lambda_{min}$=268 nm.
R$_f$ by TLC on silica gel
with chloroform/methanol 9:1=0.24.

EXAMPLE 1 dCCTTCTGGAACTG

6 μmol of DMTrdC$^{bz}$p.C$^{bz}$p.Tp.Tp.⁻ (see Example L) are dissolved in 5 ml of absolute pyridine and rendered absolute by treating several times with pyridine. Then 2.9 μmol of dC$^{bz}$p.Tp.G$^{ibu}$p.G$^{ibu}$p.A$^{bz}$p.A$^{bz}$p.C$^{bz}$p.Tp.G$_{Bz}$$^{ibu}$ (see Example N) in pyridine are added, with further drying, followed by 0.2 mmol of mesitylenesulfonyl tetrazolide. The reaction is conducted for 3 hours at ambient temperature.

Termination of the reaction and workup of the product are effected analogously to Example I.

One quarter of the crude material is detritylated analogously to Example G.

The product of the detritylation is taken up in pyridine/conc. NH$_3$ 1:1 (about 8 ml) and left to stand for 12 hours at 35° C. then for a further 6 hours at 55° C. Then all the solvents are removed by evaporation under water aspirator vacuum, in the rotary evaporator. The residue is taken up in 10 ml of water (adjusted to ph 8 using NH$_3$) and extracted three times, each time with 10 ml of ether. The aqueous phase is greatly concentrated by evaporation and added to a Biogel P 2 column (60×1.7 cm).

Elution is effected with water (pH 8). Yield: about 100 O.D.$_{260}$.

Characteristics:
UV in water: $\lambda_{max}$=265 nm; $\lambda_{min}$=235 nm.

The aqueous solution is concentrated down to about 50 μl and subjected to reverse phase HPLC. Column: μ-Bondapak C$_{18}$, Waters; eluant: 0.1 M triethylammonium acetate buffer pH 7+12–14% acetonitrile (linear gradient within 7 minutes); flow: 2 ml/minute. The tridecamer is eluted at an elution volume of 11 ml.

The product fraction is concentrated by evaporation and freed from salts using Biogel P 2, as described above, then lyophilised.

Yield: 3 O.D.
Characteristics:
UV in water: $\lambda_{max}$=260 nm; $\lambda_{min}$=233 nm.
R$_f$ by TLC on cellulose with n-propanol/NH$_3$/H$_2$O=55:10:35=0.15 based on dT.

Comparison:
R$_f$ in the same system of the unprotected pentamer=0.58, nonamer=0.28

Further characterization was effected by "fingerprint" analysis using gel electrophoresis. The gel electrophoresis pattern is shown in the FIGURE.

EXAMPLE 2 dCCTTCTGGAACTG

Prepared analogously to Example 1 by reacting 6.3 μmol of DMTrdC$^{bz}$p.C$^{bz}$p.Tp.Tp.C$^{bz}$p.Tp.⁻ with 3.4 μmol of dG$^{ibu}$p.G$^{ibu}$p.A$^{bz}$p.A$^{bz}$p.C$^{bz}$p.Tp.G$_{Bz}$$^{ibu}$ and 0.2 mmol of mesitylenesulfonyl tetrazolide. Characteristics of the unprotected fragments.

R$_f$ by TLC on cellulose
with n-propanol/NH$_3$/H$_2$O=55:10:35
of the unprotected tetramer dACTG=0.53
of the unprotected heptamer dGGAACTG=0.25

Characteristics:
UV in water: $\lambda_{max}$=260 nm; $\lambda_{min}$=233 nm.

The identification of the interferon-specific sequences in bacterial clones using the tridecanucleotide is carried out according to the following Example:

I. Preparation of the hybridization sample:

(a) 5' Terminal labelling of the tridecanucleotide with [γ-$^{32}$P] ATP and T4-polynucleotide-kinase.

The reaction is carried out in a volume of 50 μl, containing 15 μmol of tridecanucleotide, 50 mmol of tris/HCl pH 7.5, 10 mmol of MgCl$_2$, 5 mmol of DTT, 0.1 mmol of spermidine, 0.1 mmol of EDTA, 1 mCi of [γ-$^{32}$P] ATP (3000 Ci/mmol) and 2 U of T4 polynucleotide-kinase. The reaction mixture is incubated at 37° C. for 30 minutes and then the terminally-labelled tridecanucleotide was separated from the unreacted $^{32}$P-ATP by chromatography on Sephadex G 25, precipitated with alcohol and taken up again in a small volume.

(b) cDNA synthesis with the terminally-labelled tridecanucleotide as primer

The reaction is carried out in a volume of 250 μl, containing 3 μmol of terminally-labelled tridecanucleotide, 0.4 mg/ml of poly(A)+ RNA from Namalwa cells induced with Sendai virus, 0.5 mmol of dNTPs, 50 mmol of tris/Cl pH 8.3, 60 mmol of KCl, 5 mmol of DTT, 50 μg/ml of actinomycin D, 4 mmol of MgCl$_2$, 4 mmol of Na$_4$P$_2$O$_7$ and 20 U of reverse transcriptase. The reaction mixture was incubated at 37° C. for 90 minutes. The synthesised cDNA was separated from the majority of the unextended primer by chromatography on Sephadex G 50, and the RNA was removed by hydrolysis in 0.3 N sodium hydroxide solution for 1 hour at 50° C. The sample thus obtained was neutralised and used for hybridization.

II. Hybridization of bacterial colonies with the terminally-labelled specifically primed cDNA.

Bacterial clones were cultured on nitrocellulose filters and lysed using the method of Grunstein and Hogness (PNAS 72, 3961–2965, 1975). The filters were subjected to preliminary hybridization in 50% formamide, 0.6 mol of NaCl, 0.2 mol of tris/HCl pH 8, 20 mmol of EDTA, 0.02% of ficoll, 0.02% of polyvinyl pyrrolidone, 0.02% of bovine serum albumin, 0.4 mg/ml of denatured carrier DNA, 0.1% of $Na_4P_2O_7$ and 0.1% of SDS for 12 hours at 37° C., then the sample was added and incubation was continued for a further 2 days at 37° C. The quantity of sample given above was used to hybridise a filter measuring 16×25 cm (1600 clones). Any non-hybridised sample was removed by washing in 50% formamide, 30 mmol of NaCl and 3 mmol of sodium citrate. Autoradiography was effected using Kodak XR film and a Kodak X-Omatic intensifying screen.

Results

Positive clones gave a clear result after only 24 hours.

In this way, it can be shown that a synthetic oligonucleotide (13 N) which is complementary to the base sequence of a fragment of the interferon RNA (both leucocyte and fibroblast interferon) can be used to identify transformed bacterial clones which contain this sequence.

Having now fully described the invention, it will be apparent to one of ordinary skill in the art that many changes and modifications can be made thereto without departing from the spirit or scope of the invention as set forth herein.

What is claimed as new and sought to be protected by Letters Patent of the United States is:

1. A tridecadeoxynucleotide of the formula dCCTTCTGGAACTG in substantially pure form.

* * * * *